United States Patent [19]

Olson

[11] Patent Number: 5,785,700

[45] Date of Patent: Jul. 28, 1998

[54] AUTOTRANSFUSION SYSTEM WITH PORTABLE DETACHABLE VACUUM SOURCE

[75] Inventor: Daniel Henry Olson, Louisville, Ohio

[73] Assignee: Zimmer Patient Care, a Division of Zimmer, Inc., Dover, Ohio

[21] Appl. No.: 112,151

[22] Filed: Aug. 26, 1993

Related U.S. Application Data

[63] Continuation of Ser. No. 896,078, Jun. 3, 1992, Pat. No. 5,275,585.

[51] Int. Cl.[6] .................................................. A61M 5/14
[52] U.S. Cl. .......................... 604/408; 604/4; 604/319
[58] Field of Search .................................. 604/4, 403, 408, 604/410, 132, 133, 319, 415

[56] References Cited

U.S. PATENT DOCUMENTS

| | | | |
|---|---|---|---|
| 3,032,037 | 5/1962 | Huber | 128/276 |
| 3,115,138 | 12/1963 | McElvenny | 128/278 |
| 3,845,765 | 11/1974 | Ikeda | 128/277 |
| 4,048,994 | 9/1977 | Lo | 128/214 F |
| 4,058,123 | 11/1977 | May | 128/278 |
| 4,112,947 | 9/1978 | Nehring | 128/278 |
| 4,516,973 | 5/1985 | Telang | 604/319 |
| 4,573,992 | 3/1986 | Marx | 604/408 |
| 4,642,088 | 2/1987 | Gunter | 604/4 |
| 4,700,861 | 10/1987 | Neward | 215/309 |
| 4,735,613 | 4/1988 | Bellin et al. | 604/141 |
| 4,850,964 | 7/1989 | Cotter | |
| 4,869,398 | 9/1989 | Colvin et al. | 222/83 |
| 4,976,707 | 12/1990 | Bodicky et al. | 604/408 |
| 4,976,708 | 12/1990 | Oshiyama | 604/408 |
| 5,002,529 | 3/1991 | Cunningham | 604/73 |
| 5,074,839 | 12/1991 | Choksi et al. | 604/4 |
| 5,098,418 | 3/1992 | Maitz et al. | 604/319 |
| 5,112,323 | 5/1992 | Winkler et al. | 604/319 |
| 5,207,638 | 5/1993 | Choksi et al. | 604/4 |

FOREIGN PATENT DOCUMENTS

| | | | |
|---|---|---|---|
| 0 142 262 | 5/1985 | European Pat. Off. | A61M 1/00 |
| 0 048 164 | 2/1986 | European Pat. Off. | A61M 1/00 |
| 0 357 318 | 3/1990 | European Pat. Off. | |
| 1052614 | 3/1965 | United Kingdom | A61M 1/100 |
| 1 304 324 | 1/1973 | United Kingdom | A61M 1/100 |
| 1 400 139 | 7/1975 | United Kingdom | F04F 3/00 |
| 1 593 931 | 7/1981 | United Kingdom | A61M 25/00 |
| 2 079 609 | 1/1982 | United Kingdom | A61M 25/00 |
| 2 207 709 | 2/1989 | United Kingdom | A61M 1/00 |

*Primary Examiner*—John D. Yasko
*Attorney, Agent, or Firm*—Todd A. Dawson

[57] ABSTRACT

An autotransfusion system including a rigid receptacle carrying a blood collection bag internally and a manually operable portable vacuum source (MOPVS) also carried by the rigid receptacle. The system may be configured in a blood collection mode wherein the MOPVS is in flow communication with the interstitial space between the collection bag and the rigid receptacle to cause a negative pressure therein to draw blood from the patient's wound. In a reinfusion mode, the MOPVS is disconnected from the rigid receptacle and is directly connected to the drain tube leading to the patient to drain unwanted fluid from the patient's wound. The rigid receptacle is inverted and connected to a transfusion line to reinfuse the blood collected within the blood collection bag. The interstitial space is vented to ambient pressure such that the blood within the collection bag is reinfused under force of gravity alone. A hydrophobic vent is connected to the flexible collection bag to vent air collected within the bag to the interstitial space.

3 Claims, 2 Drawing Sheets

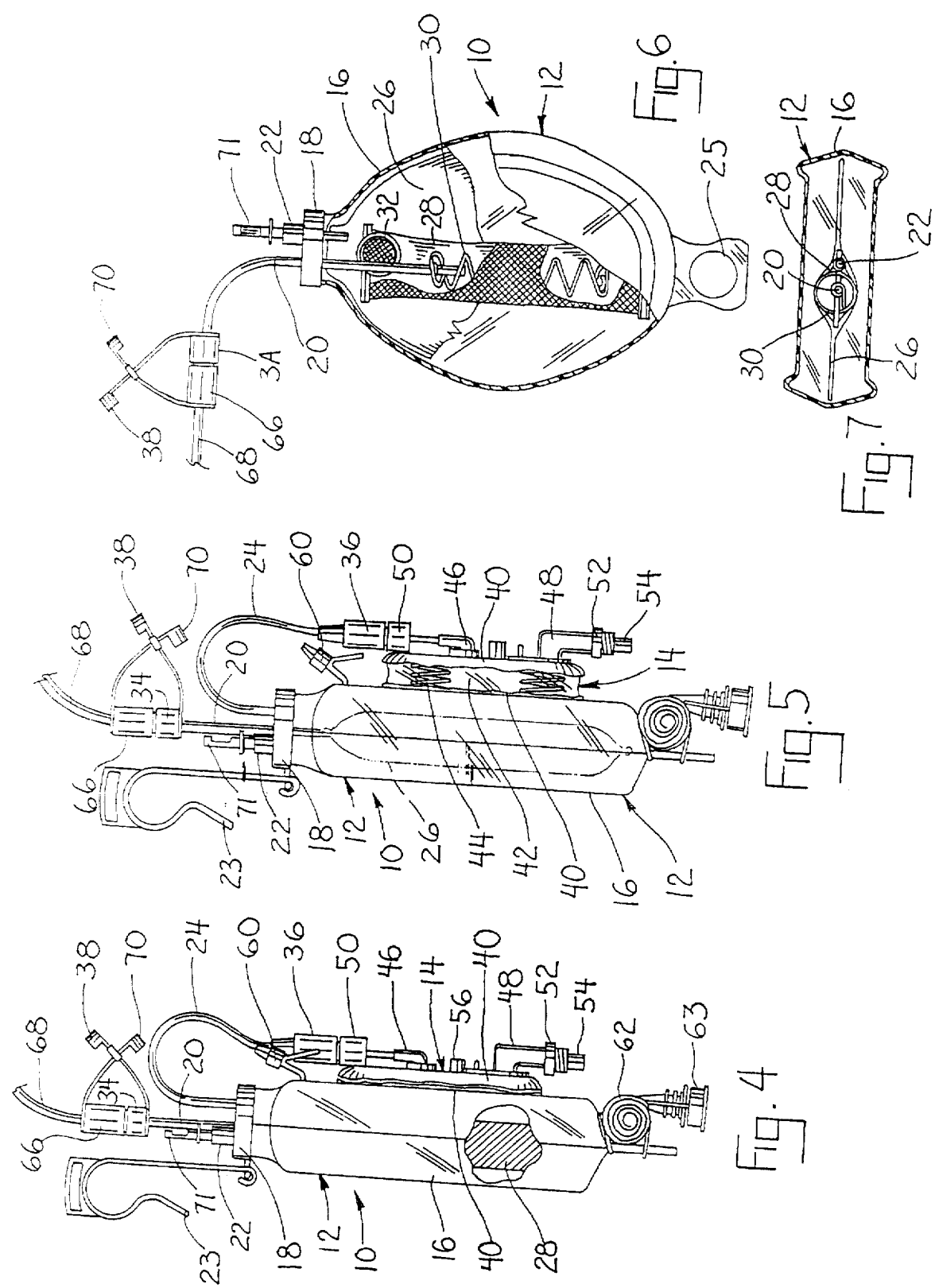

AUTOTRANSFUSION SYSTEM WITH PORTABLE DETACHABLE VACUUM SOURCE

This is a continuation of application Ser. No. 07/896,078 filed Jun. 3, 1992 now U.S. Pat. No. 5,275,585.

FIELD OF THE INVENTION

This invention relates to an autotransfusion system and has specific relevance to an autotransfusion system having a manually operable portable vacuum source which is detachable to also function as a wound drainage evacuator.

SUMMARY OF THE INVENTION

The autotransfusion system of this invention includes a blood collection bag housed within a rigid receptacle and a manually operable portable vacuum source (MOPVS) carried by the exterior of the rigid receptacle. The MOPVS includes a suction port and an exhaust port and closely resembles in construction a wound drainage device sold by Snyder Laboratories, Inc., now Zimmer Patient Care, Inc., a subsidiary of Zimmer, Inc. and patented in U.S. Pat. No. 3,115,138 incorporated herein by reference. The rigid receptacle includes an airway communicating with the interstitial space between the collection bag and the receptacle. The rigid receptacle further includes blood inlet and outlet tubes which communicate with the interior of the collection bag. The inlet tube is connected in flow communication with a filter within the collection bag to trap particulate matter therewithin. The collection bag includes a hydrophobic vent to provide an exit for air within the collection bag.

The autotransfusion system of the invention has two basic modes of operation to collect and reinfuse blood. In the collection mode, the MOPVS is connected to the rigid receptacle by common hook and loop fasteners. The airway from the rigid receptacle is connected to the suction port on the MOPVS and the blood inlet tube is connected to a drain tube leading to the closed wound of the patient. As is well known, the distal end of the drain tube is perforated and lies subcutaneously. The blood outlet tube or spike port is unconnected in this mode and is capped to protect against contamination. To begin collecting blood, the MOPVS is activated to remove air from within the interstitial space between the collection bag and rigid receptacle thereby creating a negative pressure within the rigid receptacle. The negative pressure causes the blood collection bag to expand, thereby drawing fluid from the wound through the inlet tube and filter into the collection bag. Wound air drawn into the collection bag can pass through the hydrophobic filter vent into the interstitial space. During the collection mode, it may be necessary to activate the MOPVS periodically to maintain suction. During collection, the blood drawn from the patient passes through the internal filter within the collection bag to trap clots or other particulate matter. After the collection bag is full or it is otherwise desirable to reinfuse the blood to the patient, the autotransfusion system is converted into its reinfusion mode.

In the reinfusion mode, the MOPVS is disconnected from the suction line and the blood inlet tube is disconnected from the patient tube. The MOPVS is also disconnected from the rigid receptacle. The suction port on the MOPVS is then connected to the drain tube and the MOPVS is reactivated. In the reinfusion mode, the MOPVS now functions as a wound drainage device to remove any other liquids from the wound site. When the MOPVS is sufficiently full of liquid from the wound or loses its suction, the nurse or attendant in charge connects the disposable fluid collection bag to the exhaust port spout on the MOPVS. The nurse or attendant in charge then squeezes the generally rigid walls of the MOPVS together to force the liquid out of the MOPVS and into the disposable collection bag. The disposable collection bag includes indicia to indicate the volume of fluid transferred into the bag. The disposable collection bag is then capped and disposed of in an appropriate manner. The MOPVS may again be reactivated, if necessary, to remove any remaining fluid in the wound.

To reinfuse the blood held within the collection bag in the rigid receptacle, the rigid receptacle is inverted and hung on an IV pole for gravity reinfusion. The outlet port cap is removed and a blood transfusion tubing set is inserted into to the outlet port. The IV line should include a standard transfusion filter and be primed prior to connection to the patient. The opposite end of the tube set is inserted into the vein of the patient in a common manner. With the airway tube unconnected, the interstitial space is vented to the ambient atmosphere which allows the collection bag to collapse during gravity reinfusion of the blood.

Therefore, the autotransfusion system of the invention functions as a blood collection and transfusion apparatus with its own MOPVS for collection. The MOPVS further functions as a wound drainage device for removing further liquid from the wound during transfusion.

Accordingly, it is an object of the invention to provide for a novel autotransfusion system.

Another object of the invention is to provide for a autotransfusion system which includes a manually operable portable vacuum source which serves a dual purpose of providing a local pressure source for blood collection and functions as a wound drainage device during reinfusion.

Still another object of the invention is to provide for a autotransfusion system wherein the collection bag includes a hydrophobic vent patch providing an exhaust for wound air contained within the bag.

Still another object of the invention is to provide for a autotransfusion system in which the manually operable portable vacuum source may be disconnected from the collection container and used as a wound drainage device.

Further objects of this will become apparent upon a reading of the following description taken with the accompanying drawings:

BRIEF DESCRIPTION OF THE DRAWINGS

FIG. 4 is a side elevational view of the autotransfusion system of the invention with the manually operable portable vacuum source fully collapsed. Portions are cut away for illustrative purposes.

FIG. 5 is the side elevational view of FIG. 4 with the manually operable portable vacuum source partially expanded.

FIG. 6 is a elevational view of the rigid receptacle and blood collection bag with portions sectioned for illustrative purposes.

FIG. 7 is a cross-sectional view taken along lines 7—7 of FIG. 6.

DESCRIPTION OF THE PREFERRED EMBODIMENT

Figure 1:
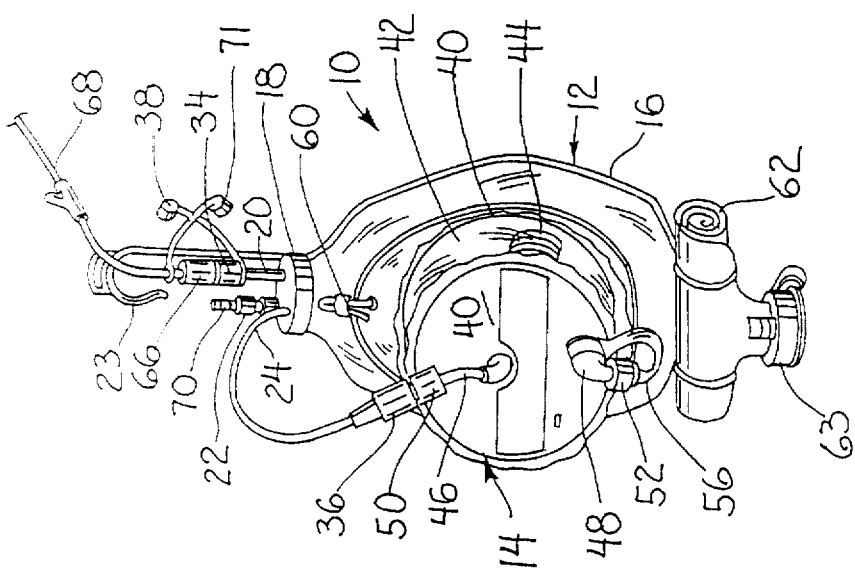
FIG. 1 is a perspective view of the autotransfusion system of the invention configured in the blood collection mode.

The preferred embodiment herein described is not intended to be exhaustive or to limit the invention to the precise form disclosed. Rather, it is chosen and described to best explain the invention so that others skilled in the art might utilize its teachings.

Referring now to the figures, autotransfusion system 10 includes as major components a blood collection receptacle 12 and a manually operated portable vacuum source (MOPVS) 14. Blood collection receptacle 12 includes a rigid receptacle 16 shaped as illustrated and including a neck portion defining an opening. The rigid receptacle opening is sealed by a lid 18 which is permanently affixed. Three openings are formed in lid 18 forming passageways for blood inlet tube 20, blood outlet tube 22 and airway 24. A hanger 23 is connected to one end of the rigid receptacle and an eyelet 25 (see FIG. 3) is formed in the opposite end of the receptacle. A blood collection bag 26 is connected to tubes 20 and 22 and is carried within the interior of receptacle 12 in flow communication with tubes 20 and 22 (See FIGS. 6 and 7). An elongated bag type filter 28 carried within bag 26 is connected to blood inlet tube 20 such that particulate matter flowing from the inlet tube can be prevented from dispersing within the interior of the collection bag. A helical spring 30 is positioned within the filter to maintain the filter in the extended position shown in the figures to prevent occlusion of the orifice of tube 20. Hydrophobic vents 32 are connected to each side of the blood collection bag over openings (not shown) to permit air contained within the bag to escape. The hydrophobic vent has a mesh size small enough to prevent liquid from exiting through its pores and micro organisms from entering the bag. Blood inlet tube 20 terminates in a threaded male connector 34. Airway 24 extends into the rigid receptacle and communicates with the interstitial space between the blood collection bag and the rigid receptacle. Airway 24 terminates in a female threaded end 36 external of the rigid receptacle. A drain cap 38 is connected to blood inlet tube 20 by a flexible strap. Cap 38 is adapted to fit within the end of male connector 34 when not in use.

MOPVS 14 includes a pair of plates 40 interconnected by a flexible side wall 42 and biased apart by helical springs 44. A suction port 46 is attached to one plate 40 in communication with the interior of the MOPVS 14. Similarly, an exhaust port 48 is connected to one plate 40 and communicates with the interior of MOPVS 14. Suction port 46 and exhaust port 48 each include a one-way valve (not shown) to permit liquid or gas flow in only one direction. Suction port 46 terminates in a threaded male connector 50 and exhaust port 48 terminates in a threaded female connector 52 having a longitudinal spout 54. A drain cap 56 is connected to exhaust port 48 by a flexible strap and is positionable on the end of spout 54 for plugging the spout when desired. A clip 60 is connected to one of the plates 40 to provide an attachment mechanism for clipping the MOPVS to a structure when configured in the wound drainage mode of FIG. 2. A disposable liquid connection bag 62 is provided which includes a threaded female 63 opening for connection to the exhaust port 48 as explained below. MOPVS 14 is connectable to the rigid receptacle by a pair of hook and loop fasteners (not shown) connected to the MOPVS and receptacle.

In use, the autotransfusion system 10 of the invention has two basic modes of operation to collect and reinfuse blood. In the collection mode, illustrated in FIGS. 1 and 4–6, the MOPVS 14 is connected to the rigid receptacle 16 by hook and loop fasteners (not shown). The female threaded end 36 of airway 24 is connected to the male threaded connector 50 of suction port 46 on MOPVS 14. The threaded male connector 34 of blood inlet tube 20 is connected to a female threaded end 66 of drainage tube 68 leading to the closed wound of the patient. Drainage tube 68 further includes a cap 70 connected to the drainage tube by a flexible strap for insertion into the threaded end 66 when not in use. As is well known, the distal end (not shown) of the drainage tube 68 is perforated and lies subcutaneously in a closed wound of a patient. The flexible straps connecting caps 70 and 38 of drainage tube 68 and blood inlet tube 20 include mutually engaging fingers (not shown) to snap lock the two straps together while the autotransfusion system is in the blood collection mode illustrated in FIGS. 1 and 4–6. By snap locking the straps together, the caps are maintained out of the way. Further, the interlocking straps constitute a method of coding the tubes for proper connection during blood collection. The capped blood outlet tube 22 or (spike port) is unconnected in this mode and is covered to protect against contamination by cap 71. The autotransfusion system 10 is hung below the level of the wound by hanger 23. To begin drawing blood from the wound, plates 40 of MOPVS 14 are squeezed together to evacuate air from the interior of the MOPVS out through exhaust port 48 such that when released, springs 44 urge the plates apart thereby drawing air in through suction port 46. With suction port 46 connected in flow communication with airway 24, the air in the interstitial space between the collection bag and rigid receptacle is substantially evacuated to cause a negative pressure within the interstitial space. This negative pressure causes the blood collection bag to attempt to expand, thereby creating suction through blood inlet tube 20 to draw blood from the wound into the collection bag. If MOPVS 14 expands fully before the collection bag is full or all the blood is drawn from the wound, MOPVS 14 may be reactivated to recreate the suction. During blood collection, air pulled into the collection bag will vent through hydrophobic vent 32 to the interstitial space due to the pressure differences between the collection bag interior and the interstitial space. If the system looses the negative pressure in the interstitial space, it may be necessary to reactivate the MOPVS.

In prior blood collection systems, if the pressure source were inadvertently activated prior to connection of the system to a drain tube, the collection bag would fill with air. The prior systems did not include a hydrophobic vent to permit the air to be drawn from within the bag. Therefore, the inadvertently pre-activated system would have a decreased volume due to the introduction of air which may render the device unusable. The autotransfusion system with the hydrophobic vents 32 connected to the collection allow air collected in the bag to be drawn through the vents and into the interstitial space. Therefore, if, the MOPVS is inadvertently activated prior to proper connection to the patients wound, the negative pressure later drawn in the interstitial space will draw the air through the vents thereby permitting the entire bag to be used for collection. As mentioned, the hydrophobic vents have a pore size so small so as to prevent micro organisms from entering the blood collection bag.

After the blood collection bag is full, or it is otherwise desirable to reinfuse the blood collected in the blood collection bag back into the patient, MOPVS 14 is disconnected from the rigid receptacle 12 and airway 24 is disconnected from suction port 46. The hook and loop fasteners are disengaged to separate the MOPVS from the rigid receptacle. During the process to convert the autotransfusion system from its blood collection mode into the reinfusion mode, the drain tube 68 leading from the patient to the blood inlet tube must be disconnected. To provide for a safe environment and limit the spillage of blood, a clamp (not shown) carried by the drain tube adjacent its female connector is engaged to clamp the flow of blood. A second clamp (also not shown) carried by the blood inlet tube is also engaged to prevent a reverse flow of blood from the blood inlet tube. After engagement of the two clamps, the connectors may be separated and capped. At this point, the rigid receptacle and the MOPVS are isolated from one another and the patient.

Figure 2:
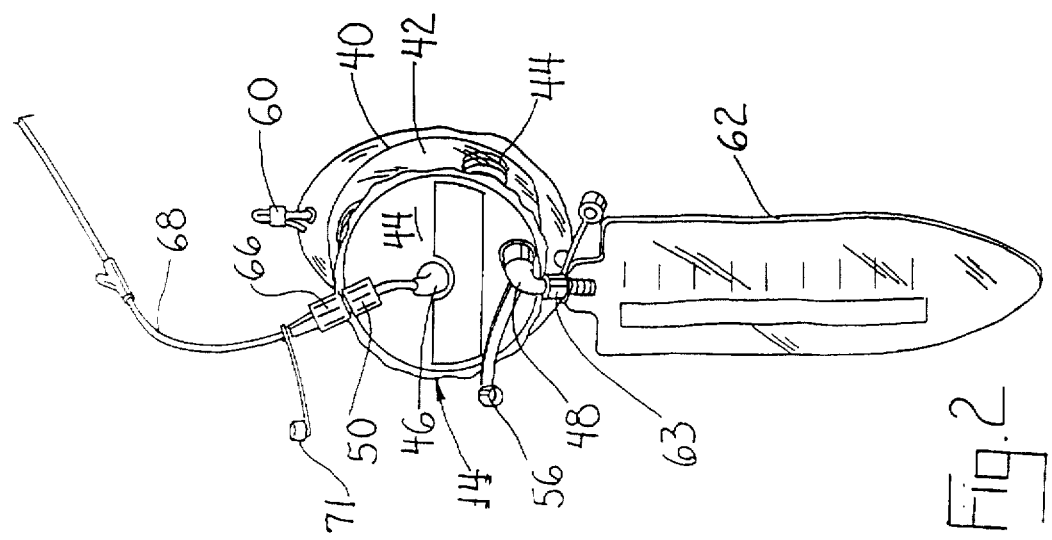
FIG. 2 is a perspective view of the manually operated portable vacuum source of the autotransfusion system configured in the fluid collection mode.

It is anticipated that even after all blood suitable for reinfusion has been drawn from the wound that additional liquid will be present which will need to be drained from the wound. Therefore, to drain any additional fluid from the wound, the suction port 46 of MOPVS is connected to the female connector 66 of the drainage tube 68. The clamp (not shown) on the drainage tube is released and the MOPVS is activated to pull a suction on the drain tube. Liquid drawn from the wound in this mode is deposited directly within the interior of the MOPVS. When the MOPVS becomes full or needs to be reactivated to continue suction, the liquid contained therein will be ejected out of the exhaust port 48. Therefore, prior to reactivation, the female connector 63 of disposable collection bag 62 is screwed onto the exhaust port 48. When the MOPVS is reactivated (plates 40 squeezed together), liquid contained within the MOPVS is transferred through the exhaust port 48 and into the disposable collection bag 62. FIG. 2 illustrates the proper orientation of the MOPVS and liquid collection bag while in a wound drainage mode.

Figure 3:
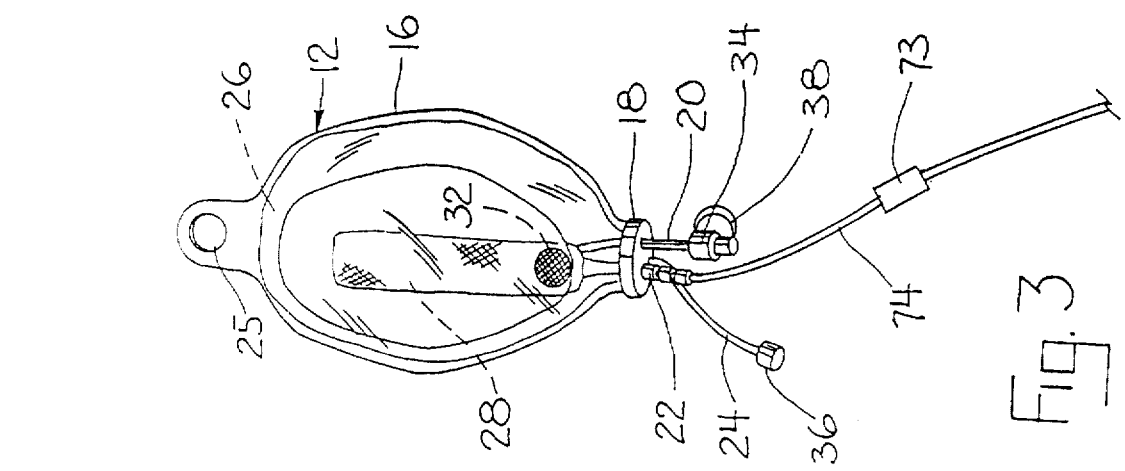
FIG. 3 is a perspective view of the rigid receptacle and blood collection bag configured in the reinfusion mode.

Referring now to FIG. 3, the rigid receptacle is illustrated in the reinfusion mode. The protective cap 71 over the blood outlet tube 22 is removed and a transfusion tube 74 having a spike (not shown) is inserted into the blood outlet tube 22. A transfusion filter 73 should be part of the transfusion line as is known in the art. It should be noted that in the reinfusion mode, airway 24 is unconnected and uncapped, venting the interstitial space to the ambient pressure as the blood drains from the collection bag solely under the force of gravity. As blood contained within the collection bag is reinfused into the patient, the collection bag is permitted to collapse. During transfusion, the rigid receptacle is inverted and suspended by a typical IV pole by opening 25. After reinfusion, the autotransfusion unit 10 is discarded in accordance with proper medical and health regulations.

Therefore, the autotransfusion system of the invention carries its own manually operable portable vacuum source to function as a blood collection and transfusion apparatus. After collection of blood, the MOPVS may be separated from the rigid receptacle and function independently as a wound drainage device.

It should be understood that the invention is not to be limited by the details above but may be modified within the scope of the appended claims.

I claim:

1. A system for collecting blood and other liquids from the wound of a patient and for reinfusing blood collected into the patient, said system comprising; a collecting means for collecting blood and being adapted to be connected in flow communication with the patient's wound, said collecting means including an outer rigid receptacle and an inner flexible bag, the rigid receptacle and the flexible bag forming an interstitial space therebetween, the flexible bag including a blood inlet port and a blood outlet port held in flow communication with an interior of the flexible bag, the inlet port being adapted for connection to drainage tubing leading to the wound, said outlet port being adapted for connection to a transfusion tube; a manually operable portable vacuum source removably carried by said collecting means by a fastener device, the manually operable portable vacuum source having an inlet being connectable to tubing in flow communication with the interstitial space of the collecting means, such that the manually operable portable vacuum source, when activated, causes a negative pressure within the interstitial space to cause said collecting bag to expand, thereby drawing blood from the wound; the system being connectable in a first mode wherein the manually operable vacuum source is carried by said collecting means and is in flow communication with the interstitial space to cause a negative pressure therein; said system being connectable in a second mode wherein said manually operable vacuum source is disconnected and disassociated from the collecting means, the interstitial space being in flow communication with ambient atmosphere and said outlet port adapted for connection to transfusion tubing, in the second mode the manually operable vacuum source is adapted for direct connection to said drainage tubing and is activated to draw fluid from said wound into the manually operable vacuum source.

2. The system of claim 1 further including a disposable fluid collection bag for connection to an exhaust port on the manually operable portable vacuum source to collect fluid from the manually operable portable vacuum source for disposal.

3. A system for collecting blood and other liquids from the wound of a patient and for reinfusing blood collected into the patient, said system comprising;

a collecting means for collecting blood and being adapted to be connected in flow communication with the patient's wound, the collecting means including a blood inlet port and a blood outlet port held in flow communication with an interior of the collecting means, the inlet port being adapted for connection to drainage tubing leading to the wound, said outlet port being adapted for connection to a transfer tube;

a manually operable portable vacuum source connected to tubing in flow communication with the interior of the collecting means such that the manually operable vacuum source when activated causes a negative pressure within the collecting means to thereby draw blood from the wound;

the system being connectable in a first mode wherein the manually operable vacuum source is in flow communication with the interior of the collecting means to cause a negative pressure therein;

said system being connectable in a second mode wherein the interior of the collecting means is in flow communication with ambient atmosphere and said outlet port adapted for connection to transfusion tubing, the manually operable portable vacuum source is adapted for direct connection to said drainage tubing and is activated to draw fluid from said wound into the manually operable vacuum source.

\* \* \* \* \*